March 12, 1974 L. K. WILEMAN Plant Pat. 3,520
POMEGRANATE TREE
Filed Nov. 10, 1972
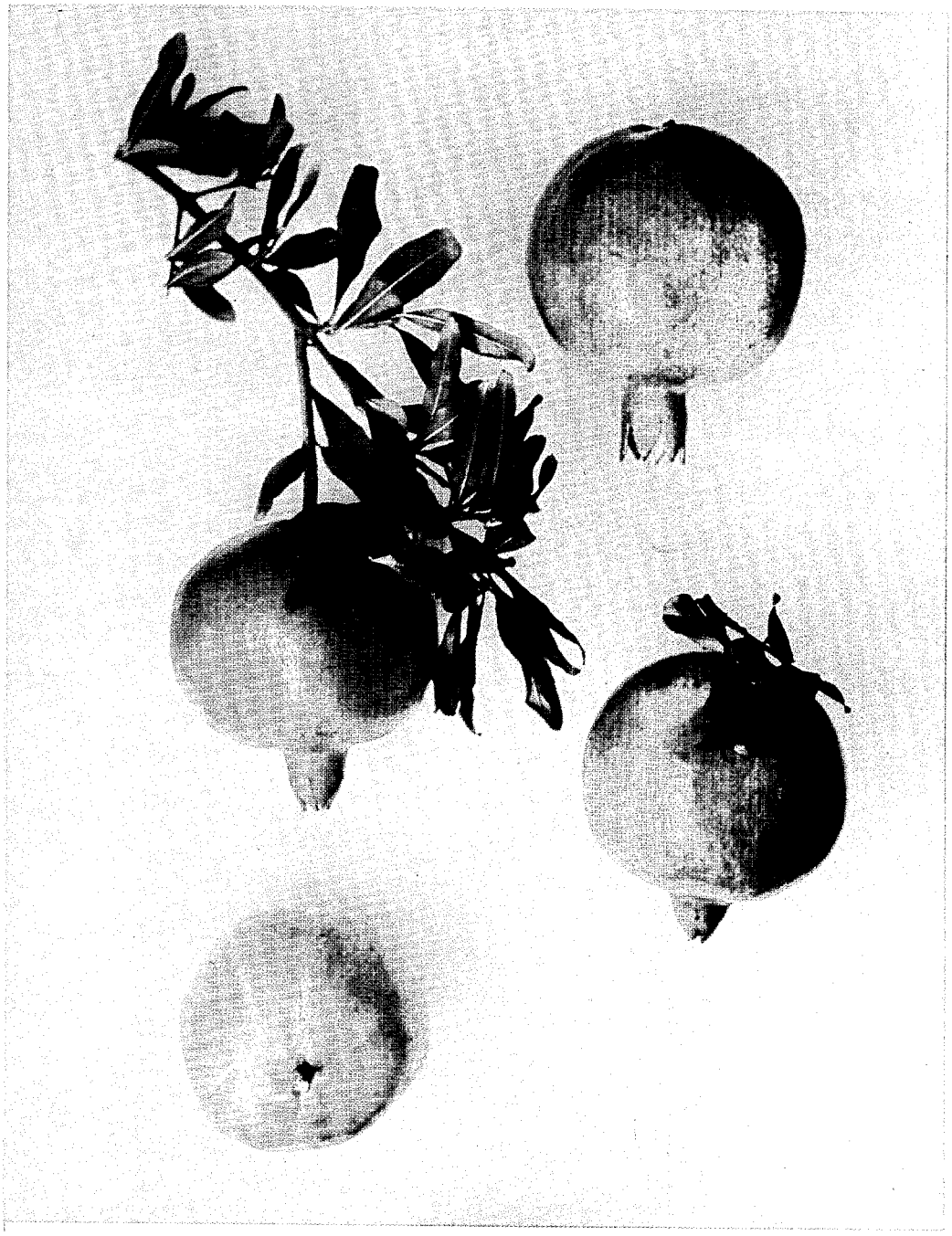

United States Patent Office

Plant Pat. 3,520
Patented Mar. 12, 1974

3,520

POMEGRANATE TREE

Leonard K. Wileman, 13136 Avenue 400,
Cutler, Calif. 93615

Filed Nov. 10, 1972, Ser. No. 305,495
Int. Cl. A01h 5/03
U.S. Cl. Plt.—33 1 Claim

ABSTRACT OF THE DISCLOSURE

A rapid-growing pomegranate tree which is of medium size, vigorous, spreading, round-topped, foliated with small lanceolate leaves, blooms late with large, orange-red, fertile flowers, and is a regular and productive bearer of large, thin-skinned, round-oblate fruit symmetrical and uniform in shape, and having a deep red exterior color.

Origin of the variety.—The present variety of pomegranate tree was discovered by me growing in an orchard of Wonderful (unpatented) pomegranate trees located on a ranch in Tulare County, California, during a harvest of such orchard under my direction as field manager. As pomegranate nursery stock is almost entirely propagated by cuttings, it is reasonable to assume that the tree, of my discovery, is probably a mutation.

Asexual reproduction of the variety.—Subsequent to my discovery of the present variety of pomegranate tree, and recognition by me of its desirable characteristics for commercial growing to provide a marketable fruit both as a food and for ornamental display, I asexually reproduced the variety, on my ranch located near Cutler, Tulare County, Calif., by scion grafting as well as by rooting hardwood cuttings. In maturity, such reproductions ran true to the originally discovered tree in all respects.

Summary of the variety.—The present variety of pomegranate tree is, in its characteristics, of medium size, vigorous, spreading, round-topped, foliated with small lanceolate leaves, blooms late with large, orange-red, fertile flowers, and is a regular and productive bearer of large, thin-skinned, round-oblate fruit symmetrical and uniform in shape, and having a deep red exterior color.

The present variety of pomegranate tree is further characterized by general resemblance, in tree and fruit, to the Wonderful, but is distinctive, in comparison, by foliage which is slightly less green but more vigorous; by fruit which at harvest maturity has a deep red exterior color rather than the yellowish-straw ground color (with a slight blush of red) of the Wonderful; and by fruit which is at harvest maturity about two weeks earlier than the Wonderful. While both the present variety and the Wonderful attain the requisite acid factor (the test of palatability) at approximately the same time, only the present variety is then in full color and ready to harvest, and which is accomplished in one picking. Thus, the present variety can be harvested earlier while presenting a very attractive appearance by virtue of its deep red exterior color. Also, by reason of the earlier harvest, the fruit of the present variety is less subject to damp fall weather and attendant splitting of the skin and bursting of the fruit.

The present variety of pomegranate tree is further characterized, in comparison to the Granada (U.S. Plant Pat. No. 2,618), by a harvest period which is about three weeks later, but with larger fruit, than said Granada.

Brief description of the drawing.—The drawing is an illustration, by photographic reproduction in color, of a twig with leaves and an attached fruit, and other fruit detached.

Description of the variety.—The botanical details of this new and distinct variety of pomegranate tree—with color definitions (except those in common color terms) referenced to Maerz and Paul Dictionary of Color—are as follows:

Tree:
- *Size.*—Medium.
- *Vigor.*—Vigorous.
- *Growth.*—Spreading, drooping, rapid.
- *Form.*—Round-topped.
- *Production.*—Productive.
- *Bearing.*—Regular bearer.

Trunk:
- *Size.*—Medium.

Branches:
- *Size.*—Medium.
- *Texture.*—Medium zigzag.
- *Color.*—Brown.

Lenticels:
- *Number.*—Numerous.
- *Size.*—Small.

Leaves:
- *Size.*—Small. Narrow—⅝"–¾"; long—2½"–2¾".
- *Form.*—Lanceolate, taper-pointed.
- *Thickness.*—Thin.
- *Color.*—Top Side—Medium green (22–L–9). Under side—Lighter green (21–L–9).
- *Texture.*—Smooth.
- *Margin.*—Repand. Very finely serrate, almost smooth.
- *Petiole.*—Short—3/16". Slender.

Flowers:
- *Blooming period.*—Late. Date of first bloom: Mar. 22, 1972. Date of full bloom: Mar. 30, 1972.
- *Size.*—Large.
- *Color.*—Orange-red.
- *Fertility.*—Fertile.

Fruit:
- *Length of season.*—One week. Date of first picking: Sept. 14, 1972. Date of last picking: Sept. 21, 1972.
- *Retention.*—Hangs well.
- *Size.*—Large. Diameter axially 2¾"–3¼". Transversely in suture plane—2¾"–3½". Variable.
- *Form.*—Round—oblate. Symmetrical. Uniform.
- *Stem.*—Short. Thick.
- *Calyx.*—Open, medium size. Lobes: Separated at base; Medium length; acute.
- *Basin.*—Wide. Smooth.

Skin:
- *Thickness.*—Thin.
- *Texture.*—Smooth, glossy.
- *Color.*—Ground color—Marguerite yellow (10–C–1), almost completely overspread with deep red (4–L–6 to 6–L–6), with some mottling and streaking.
- *Dots.*—Numerous, small, russet, areolar.

Flesh:
- *Texture.*—Membranous—firm.
- *Color.*—Marguerite yellow (10–C–1).
- *Arils.*—Multitudinous, with small, plump, whitish seeds. purple-red (55–J–7). Firm. Crisp. Subacid. Juicy. Sprightly—tart.
- *Eating quality.*—Very good.
- *Calyx tube.*—Length: Medium. Width: Medium. Form: Tubular.

Use: Kitchen, market, home, ornamental.
Keeping quality: Good.
Shipping quality: Good.
Resistance to insects and diseases: No unusual susceptibilities noted.

The pomegranate tree and its fruit herein described may vary in slight detail due to climatic and soil conditions under which the variety may be grown; the present description being of the variety as grown in the Central Valley of California.

I claim:

1. A new and distinct variety of pomegranate tree, substantially as illustrated and described, which is of medium size, vigorous, spreading, round-topped, foliated with small lanceolate leaves, blooms, late with large, orange-red, fertile flowers, and is a regular and productive bearer of large, thin-skinned, round-oblate fruit symmetrical and uniform in shape, and having a deep red exterior color; the variety, in comparison to the Wonderful, has foliage which is less green but more vigorous, and bears fruit which at harvest maturity is said deep red exterior color, and which harvest maturity is about two weeks earlier; and the variety, in comparison to the Granada, bears larger fruit which is at harvest maturity about three weeks later.

No references cited.

ROBERT E. BAGWILL, Primary Examiner